United States Patent
Vogtherr et al.

(10) Patent No.: US 9,850,924 B2
(45) Date of Patent: Dec. 26, 2017

(54) ADAPTER DEVICE FOR AN OPERATING TABLE

(71) Applicant: Aesculap AG, Tuttlingen (DE)

(72) Inventors: Robert Vogtherr, Tuttlingen (DE); Thomas Beck, Durchhausen (DE); Pedro Morales, Tuttlingen (DE)

(73) Assignee: Aesculap AG (DE)

( * ) Notice: Subject to any disclaimer, the term of this patent is extended or adjusted under 35 U.S.C. 154(b) by 0 days.

(21) Appl. No.: 14/888,135

(22) PCT Filed: May 15, 2014

(86) PCT No.: PCT/EP2014/059934
§ 371 (c)(1),
(2) Date: Oct. 30, 2015

(87) PCT Pub. No.: WO2014/187721
PCT Pub. Date: Nov. 27, 2014

(65) Prior Publication Data
US 2016/0076566 A1 Mar. 17, 2016

(30) Foreign Application Priority Data
May 24, 2013 (DE) .......................... 10 2013 105 374

(51) Int. Cl.
*A47C 21/00* (2006.01)
*F16B 2/06* (2006.01)
(Continued)

(52) U.S. Cl.
CPC .............. *F16B 2/065* (2013.01); *A47C 21/00* (2013.01); *A61B 90/50* (2016.02); *A61G 13/101* (2013.01);
(Continued)

(58) Field of Classification Search
CPC ...................................................... A47C 21/00
(Continued)

(56) References Cited

U.S. PATENT DOCUMENTS 3,528,413 A   9/1970 Aydt
4,796,846 A * 1/1989 Meier .................... A61B 17/02
                                                    248/286.1
(Continued)

FOREIGN PATENT DOCUMENTS

CN        2715739 Y      8/2005
CN        200951166 Y    9/2007
(Continued)

OTHER PUBLICATIONS

German Search Report for German Application No. 10 2013 105 374.2 dated Jan. 9, 2014, including partial translation.
(Continued)

*Primary Examiner* — Fredrick Conley
(74) *Attorney, Agent, or Firm* — RatnerPrestia

(57) ABSTRACT

An adapter device for detachably fastening instruments and equipment to a side rail of an operating table includes a clamping device by means of which the adapter device can be clamped to the side rail of the operating table, a longitudinal profile onto which the instruments and equipment can be detachably fastened, and a joint having at least one pivot axis formed between the clamping device and the longitudinal profile so that the longitudinal profile is pivotable relative to the clamping device about the pivot axis of the joint.

14 Claims, 4 Drawing Sheets

Figure 1:
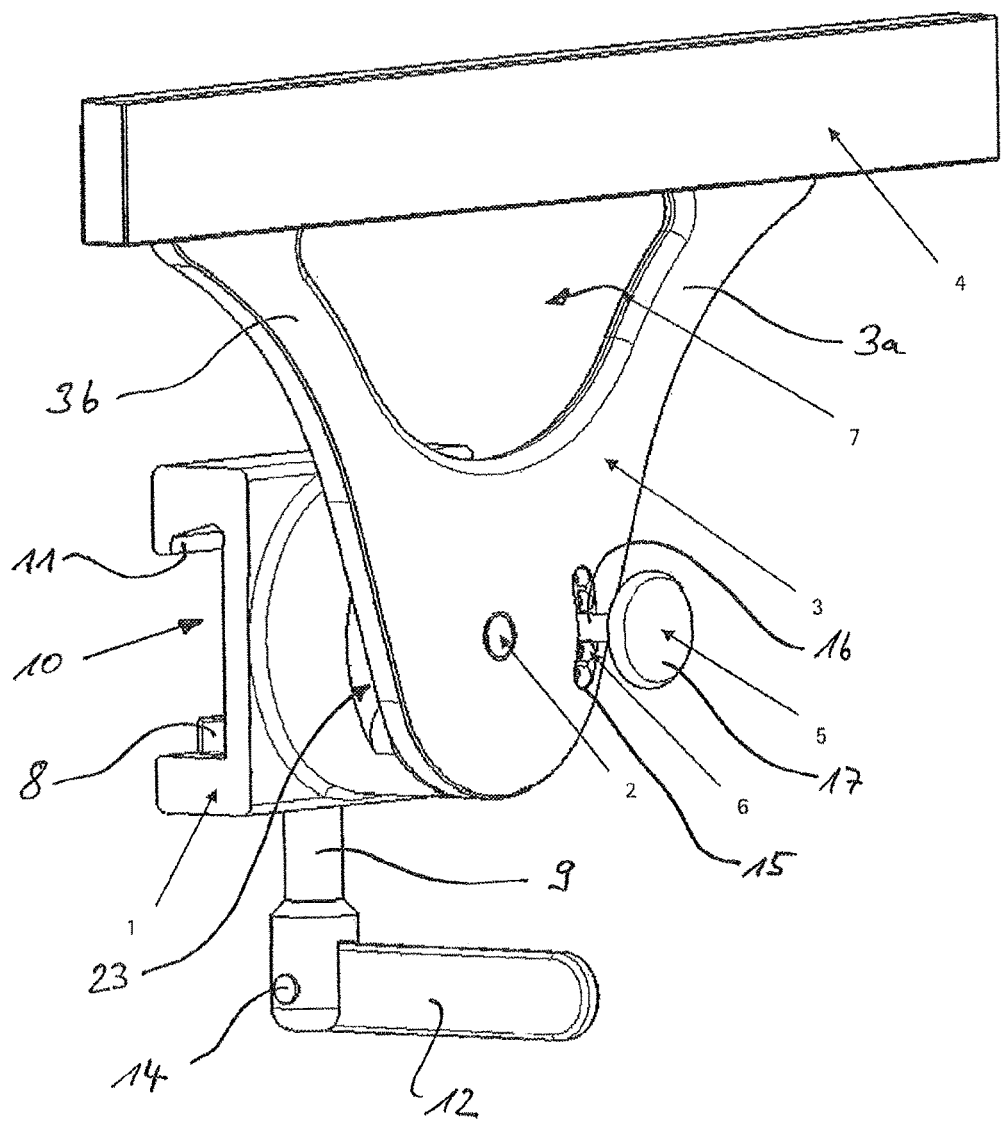

(51) Int. Cl.
  *A61G 13/10*  (2006.01)
  *F16C 11/10*  (2006.01)
  *F16M 13/02*  (2006.01)
  *A61B 90/50*  (2016.01)
  *A61B 90/57*  (2016.01)

(52) U.S. Cl.
  CPC ............... *F16B 2/06* (2013.01); *F16C 11/10* (2013.01); *F16C 11/103* (2013.01); *F16M 13/022* (2013.01); *A61B 2090/571* (2016.02); *A61G 2203/78* (2013.01)

(58) Field of Classification Search
  USPC ..... 5/600, 621, 646, 658; 248/286.1, 288.51
  See application file for complete search history.

(56) References Cited

U.S. PATENT DOCUMENTS

| | | | |
|---|---|---|---|
| 6,023,800 | A | 2/2000 | Stickley |
| 2008/0034502 | A1 | 2/2008 | Copeland |
| 2012/0304383 | A1 | 12/2012 | Marugg |
| 2012/0318278 | A1 | 12/2012 | Aboujaoude |
| 2013/0019883 | A1 | 1/2013 | Worm |
| 2013/0092058 | A1 | 4/2013 | Slagle |
| 2013/0123911 | A1 | 5/2013 | Chalekian |
| 2014/0296650 | A1 | 10/2014 | Weisshaupt |

FOREIGN PATENT DOCUMENTS

| | | |
|---|---|---|
| CN | 101849132 A | 9/2010 |
| CN | 102551983 A | 7/2012 |
| DE | 403952 | 10/1924 |
| DE | 202009007202 | 8/2009 |
| DE | 102009021222 | 11/2010 |
| WO | 2013060581 | 5/2013 |

OTHER PUBLICATIONS

International Search Report for International Application No. PCT/EP2014/059934 dated Aug. 18, 2014.

Chinese Office Action with English language translation for Application No. 201480029984.4, dated Dec. 21, 2016, 12 pages.

\* cited by examiner

ADAPTER DEVICE FOR AN OPERATING TABLE

RELATED APPLICATIONS

The present application is the U.S. National Phase entry of International Application No. PCT/EP2014/059934, filed May 15, 2014, which claims the benefit of priority of German Application No. DE 10 2013 105 374.2, filed May 24, 2013. The contents of International Application No. PCT/EP2014/059934 and German Application No. DE 10 2013 105 374.2 are incorporated by reference herein in their entireties and for all purposes.

FIELD

The present invention relates to an adapter device for detachably fastening holding instruments, auxiliary instruments, instrument feeding trays and the like to a side rail of an operating table.

BACKGROUND

In the following description, holding instruments, auxiliary instruments, instrument feeding trays and the like shall be briefly referred to as auxiliary equipment.

For surgical interventions on a patient lying on an operating table auxiliary equipment is usually arranged and fastened on standardized side rails of rectangular cross-section provided laterally at the operating table. Modern operating tables are divided into plural table segments which can be adjusted and positioned relative to each other so that the operating table can be adapted to the type of surgical intervention, the particular operating situation as well as the size and shape of the patient. For example, cardio-surgical interventions frequently require the patient's thorax to be positioned higher than the legs and the pelvis at a defined angle. This is achieved by tilting head-side segments of the operating table.

The side rails of the operating table are appropriately segmented just as the table itself. As a rule, a side rail segment to which auxiliary equipment can be fastened is assigned to each table segment. Adjustments of a table segment produce corresponding changes in position of the respective side rail segments and thus also of the auxiliary equipment arranged there. Under certain circumstances it may then be a drawback that the latter is no longer located in the previous carefully adjusted position.

From the state of the art devices are known by which afore-mentioned auxiliary equipment can be arranged on and fastened to an operating table. Additional rails that are fastened to a side rail of the operating table and, apart from the latter, offer additional options for fixing accessories, are rigidly connected to the table rail and therefore follow each change of position. Furthermore, vises are known which are adapted to be clamped to a table rail and which have a ball joint. Said devices are used, e.g. as infusion holder or for an instrument feeding tray. In this case, via the ball joint a vertical alignment of the holder and, resp., a horizontal alignment of the instrument feeding tray is possible.

From DE 403952 a coupling device for connecting an instrument tray to an operating table or the like is known in which an instrument tray is movably fastened by a clamp to a longitudinal rail of the operating table. The clamp carries a height-adjustable supporting rod including a cardan joint. A rod which on one side supports the instrument tray and on the opposite side carries a counter-weight is rotatable in the cardan joint. The counter-weight keeps the instrument tray balanced in each position of the operating table.

The prior art devices disadvantageously are either vises with adjusting options which are adapted to accommodate only one piece of auxiliary equipment at a time, however, or are auxiliary rails which, although adapted to support plural pieces of auxiliary equipment, are rigidly arranged relative to the respective operating table segment and do not offer any adjusting or adapting options. When plural pieces of auxiliary equipment are adjustably arranged by means of vises, it is a drawback that each piece of auxiliary equipment has to be individually adapted to the new configuration of the table when the operating table or individual segments thereof have been adjusted. This is time-consuming and impractical, especially when the adjustments of the operating table are required during operation.

Finally operating tables used to be covered by sterile cloths so that in this way also the table rails are covered by the cloths. This impedes exact positioning and fastening of auxiliary equipment at the covered table rail.

SUMMARY

Starting from the afore-described state of the art, the object underlying the invention is to provide an adapter device for detachably mounting auxiliary equipment on one of the side rails of an operating table which allows facilitated handling. Preferably an adapter device is to be provided which can be used universally for common auxiliary equipment, which is adapted to accommodate a plurality of auxiliary equipment and fasten the same to an operating table, which can be easily, safely, exactly and quickly adjusted and adapted as well as aligned by a user and which, in the case of changes in position at the operating table or at particular segments thereof, allows quick alignment of the auxiliary equipment disposed there.

The invention combines the advantages of an adaptable auxiliary rail with those of a common vise and, when used together with an operating table having segmented side rails, facilitates compensation of the angular adjustments of segments of an operating table. In the simplest configuration the joint has one single pivoting degree of freedom with a possibility of pivoting the longitudinal profile in a vertical plane. The longitudinal profile permits to arrange a plurality of auxiliary equipment thereon and can be easily disposed on a standardized side rail of the operating table by means of the clamping device. Due to the joint formed between the clamping device and the longitudinal profile, the longitudinal profile can be advantageously adapted and adjusted along with all pieces of auxiliary equipment arranged thereon. If, for example, one segment of an operating table is adjusted, all pieces of auxiliary equipment arranged on said segment can be aligned by one single and simple operating step uniformly, simultaneously, quickly and easily adapted analogously to the new position of the segment. The pieces of auxiliary equipment are movably accommodated on the longitudinal profile preferably in the longitudinal direction thereof so that they can be easily positioned relative to each other. Apart from the auxiliary equipment, also further adapters can be arranged on the longitudinal profile. In this way high flexibility of the adapter device according to the invention is permitted. In other words, the adapter device according to the invention includes a mounting part, for example in the form of said clamping device or screw clamp to which an operating table rail simulating member is hinged via a lockable hinge. Consequently, the operating table rail simulating member exhibits the longitudinal profile simulating the operating table rail which in the mounted state is arranged above a sterile cloth in the sterilizing room and thus is perfectly visible. The lockable hinge is further located on one side of the clamping device which faces away from the clamping-engaging means and thus is equally located above the sterile cloth in the sterilizing room. Thus, the longitudinal profile can be pivoted during an operation in the form of a pitch related to the extension of the longitudinal profile.

The joint may be configured to be lockable in most various ways. In particular, the joint may be lockable and locked by means of form closure, preferably in that a locking member engages in a locking recess or in one of plural locking recesses of the joint. A positive locking option can be advantageously operated in a quick, simple and reliable manner. The locking member may be a spring-loaded tension bolt which in the idle position into which it is biased engages in one of the locking recesses and can be released from the locking recess by manually applied tension against the spring load.

As an alternative, the joint may be lockable or locked by force closure, preferably in that a tightening screw clamps the joint. Locking by force closure offers the advantage of very fine and individually selectable options of adjustment.

The joint of the adapter device according to the invention may as well be equipped with plural degrees of freedom of movement, especially in the form of a pivot or ball joint. The selection is made according to the number of desired degrees of freedom for adjustments of the adapter device.

According to an embodiment of the invention, the clamping device forms a first part of the joint, while the longitudinal profile or a unit connected to the longitudinal profile forms the counterpart interacting with the first joint member. In this way, the adapter device is very compact and stable and can be arranged on the operating table with hardly any restrictions of accessibility of the same.

The clamping device can be configured especially in the form of a vise or can be a vise. Advantageously, a vise can be arranged on a side rail of an operating table. Usually it includes a recess or groove into which a common side rail can be easily inserted. The recess or groove may be configured to have an undercut or to have projections encompassing a side rail (e.g. dovetail cross-section) so that the side rail can be accommodated safely and in the correct position. The side rail has to be clamped in the recess or groove by means of a clamping device, e.g. in the form of a tightening screw or tightening lever or else a pressure plate actuated in this way. A pressure plate reduces the surface pressure acting on the side rail so that the formation of dents can be largely prevented.

In particular when the clamping device forms a first part of the joint and thus the pivot axis is provided substantially level with the side rail of the operating table, it is of particular advantage when the adapter device comprises an arm or extension which then supports the longitudinal profile at a distance (height distance) from the pivot axis of the joint. Moreover the arm can be used to compensate for the height of operating table lining. By appropriately designing the arm and, resp., the connection between the arm and the longitudinal profile it is moreover possible to influence the lateral distance between the operating table and the longitudinal profile by simple measures.

It is of particular advantage that the arm serves as a handle for adjusting or adapting the adapter device. Furthermore, it can especially have a recess or a free space adapted to be used as a handle. Of particular advantage the arm may be designed to be angular having two arm elements. Each arm element may be arranged, on the one hand, on the joint and, on the other hand, on the longitudinal profile. In this embodiment the longitudinal profile is secured and supported by the arm in an especially stable manner and the arm is simply shaped as a handle, which facilitates easy cleaning. In order to provide for convenient handling and to minimize a risk of injury the edges of the adapter device, especially the edges of the arm configured as a handle, may be rounded off.

According to another embodiment, the cross-section of the longitudinal profile may correspond to the cross-section of a standardized side rail of an operating table. This ensures that common auxiliary equipment for side rails can also be used jointly with the adapter device according to the invention. Alternatively, the cross-section of the longitudinal profile may be round. In both cases the longitudinal profile may include limit stops preventing the auxiliary equipment arranged thereon from being inadvertently released, for example during alignment in the longitudinal direction of the longitudinal profile.

Longitudinal profiles having a round cross-section are advantageously configured to be flattened in portions, especially at the end side, or to have at least one recess so as to facilitate the arrangement and release of auxiliary equipment on/from the same. The auxiliary equipment then can be combined with the longitudinal profile according to the lock-and-key principle in the area of the flattening or recess, i.e. it can be arranged on the same or removed therefrom. Outside a flattened portion it is not possible to arrange or remove auxiliary equipment, which increases the safety during handling.

BRIEF DESCRIPTION OF THE DRAWING FIGURES

Figure 2:
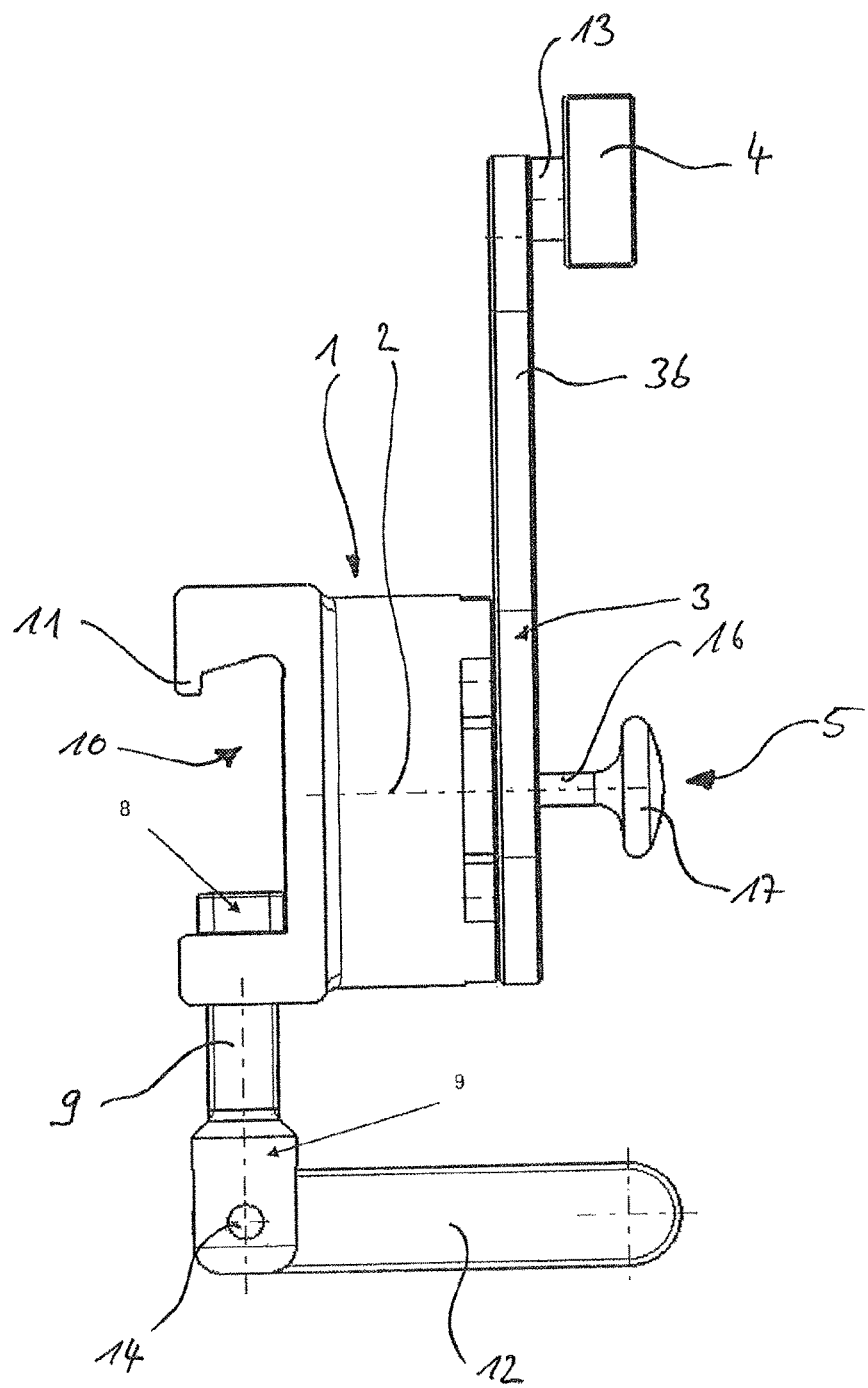
Figure 3:
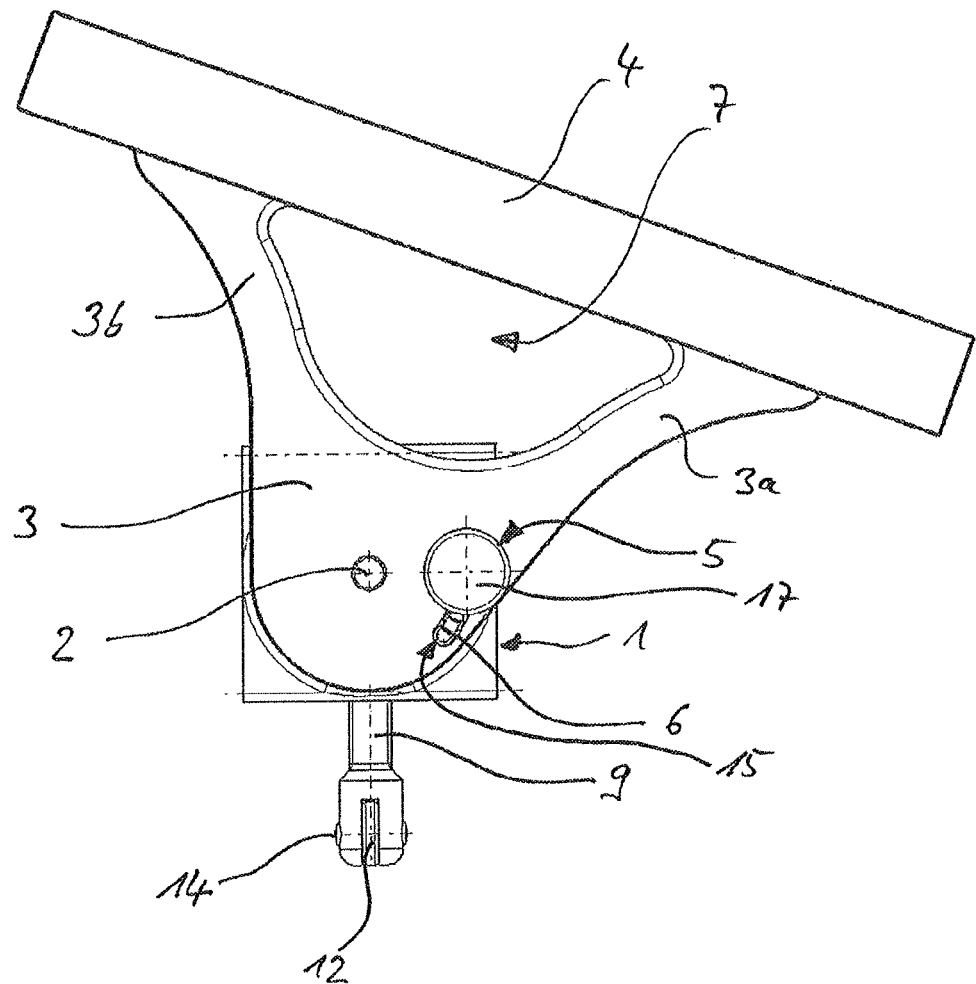
Figure 4:
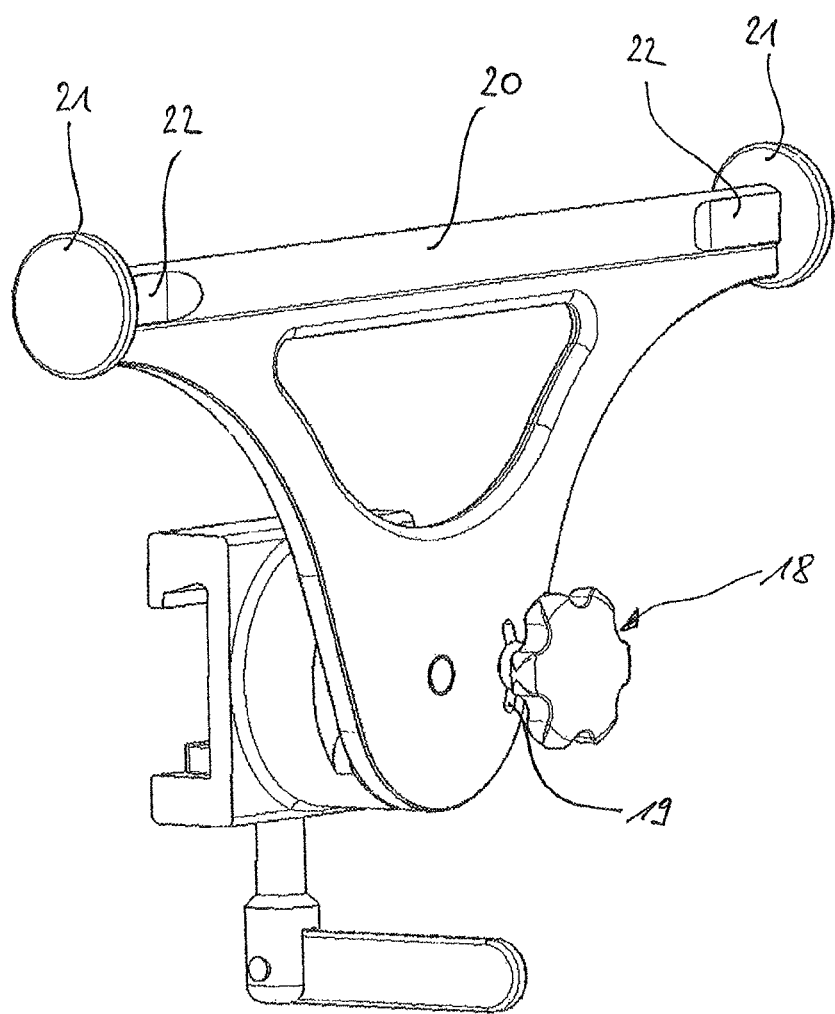

Further features and advantages of the present invention will be resulting from the following exemplary description of an especially preferred embodiment of the invention by way of the Figures, in which:

FIG. 1 shows a first embodiment of an adapter device according to the invention in a perspective view, FIG. 2 shows the adapter device of FIG. 1 in a side view, FIG. 3 shows the adapter device of FIGS. 1 and 2 in a top view at a position pivoted vis-à-vis FIGS. 1 and 2, and FIG. 4 shows another embodiment of an adapter device according to the invention in a perspective view.

DETAILED DESCRIPTION

The adapter device shown in FIGS. 1, 2 and 3 includes a vise 1 as a clamping device by which the adapter device can be clamped to a side rail of an operating table not shown in the Figures. The vise 1 includes a groove 10 via which it can be slipped onto the side rail. The groove 10 is configured, on one of its side flanks, to have an undercut which is formed by a projection or ledge 11 encompassing a side rail inserted in the groove 10. At the side flank of the groove 10 opposing said projection a pressure plate 8 is arranged. Said pressure plate is adapted to be tensioned against a side rail of an operating table inserted in the groove 10 by means of a tightening screw 9 so that the pressure plate 8 is forced against a side rail by tightening the tightening screw 9, thus causing the vise 1 to be tightly clamped onto the same. By releasing the tightening screw 9 the pressure plate 8 is unfastened vis-à-vis the side rail, and the vise can be displaced on the side rail or can be detached from the same. The use of the pressure plate 8 serves for reducing the surface pressure onto the side rail and the formation of dents.

In order to permit and to facilitate user-side handling of the tightening screw 9 especially without using tools the tightening screw is equipped with a lever 12 by which the tightening screw can be easily and safely tightened and released. The lever 12 is pivoted at the tightening screw 9 by means of a pin 14 so that it can be aligned transversely to the longitudinal axis of the tightening screw 9 to tighten or release the latter, or otherwise it can be brought into a position which does not impede the handling of the adapter device and is orientated substantially in the longitudinal direction of the tightening screw 9. Instead of the tightening screw 9, also a quick-clamping element can be employed, as it is known from cycling for fastening wheels in wheel forks.

In the vise 1 a pivot axis 2 is arranged which is perpendicular to the plane of the side rail positively interacting with the groove 10, i.e. perpendicular to the groove base. The pivot axis protrudes on the side of the vise 1 facing away from the groove 10 over said vise and supports an arm 3. The arm 3 is accommodated on the pivot axis 2 to be rotatable around the same so that a joint 24, in this case in the form of a pivot joint/hinge, is formed between the arm 3 and the vise 1. Consequently, the vise 1 and the arm are pivoting relative to each other about the pivot axis 2.

For configuring a ball joint the end of the pivot axis 2 may be in the form of a ball which is received in a corresponding spherical surface of the arm 3 so that the arm 3 is adapted to pivot not only about the pivot axis 2 with one degree of freedom, as shown in the Figures, but about the ball with three degrees of freedom.

The arm 3 includes two arm elements or braces 3a and 3b. They are angled relative to each other and between them form a V-shaped free space 7 into which a user can engage during handling and especially during swiveling and adjusting the adapter device and can make use of one of the arm elements 3a, 3b or both of them as a handle. For this purpose, the edges of the arm elements 3a, 3b directed to the free space 7 are rounded off.

At their ends facing away from the pivot axis 2 the two arm elements 3a, 3b support a longitudinal profile 4 serving as an additional rail. Said longitudinal profile may be connected in any appropriate manner to the arm elements 3a, 3b or may be formed integrally with the same. FIG. 2 illustrates that the longitudinal profile 4 is arranged outside the plane of the arm 3 on the side thereof facing away from the vise 1. Between the longitudinal profile 4 and each arm element 3a, 3b a spacer 13 is arranged which ensures sufficient distance of the longitudinal profile 4 from the plane of the arm 3 so that auxiliary equipment can be arranged and adjusted on the longitudinal profile 4 and can be displaced along the latter without being restricted by the arm elements 3a, 3b. Due to the fact that the arm 3 carries the longitudinal profile 4 at a distance from the pivot axis 2 in the orthogonal direction, the height of an operating table lining, i.e. the distance from the lying area for a patient from the side rail of the operating table, can be compensated.

The length of the longitudinal profile 4 is referred to as LL. Said length LL is preferably maintained somewhat shorter than the length LS of a side rail segment 25 indicated by dot-dashed lines to which the adapter device is fastened. This geometrical adaptation ensures that the neighboring rails do not interfere with each other during relative pivoting movements.

In the shown embodiments the longitudinal profile 4 has a cross-section corresponding to the standardized cross-section of a common side rail of an operating table as regards dimensions and geometry. In this way common auxiliary equipment may be arranged on the longitudinal profile 4.

A sliding surface of the vise 1 facing the arm 3 is provided with the reference numeral 26 (cf. FIG. 2). Said sliding surface 26 is provided with recesses 23, preferably in the form of cutouts, as visible from FIGS. 1 and 4, so as to improve and facilitate cleaning of said sliding surface.

The adapter device shown in FIGS. 1 to 3 can be locked by means of a bolt 5 at a desired position. The locking is performed by form closure of the bolt with engagement structures 6 formed in the arm (or in the vise 1). In the arm 3 a continuous bent slot hole 15 is formed the radius of curvature of which corresponds to the distance of the center line of the slot hole 15 from the central axis of the pivot axis 2 and the center of curvature of which coincides with said central axis. The bolt 5 is tightly connected via a shank not shown in the Figures to the vise 1, and is, for example, screwed into the same. On said shank a sleeve 16 enclosing said shank is provided which is widened at its end facing away from the vise 1 toward an actuating button 17. The outer dimension of the sleeve 16 is larger than that of the shank.

The shank and the sleeve 16 of the bolt 5 are biased against each other by means of a spring not shown in the Figures so that the sleeve 16 is urged by the actuating button 17 toward the vise 1. The outer dimension of the sleeve 16 is adjusted to the inner dimension of the engagement structures 6 so that a form closure is produced there between, when the sleeve 16 engages in one of the engagement structures 6. Due to said form closure the arm 3 is locked vis-à-vis the vise 1. The spring bias constantly urges the sleeve 16 of the bolt 5 into said form closure. In order to release the locking, a user grasps the actuating button 17 of the bolt 5 and pulls it away from the vise 1 against the bias of the spring. The sleeve 16 detaches from the engagement structures 16 and, because of the smaller outer dimension of the shank, the arm 3 may be pivoted about the pivot axis 2. Based on the defined distances of the engagement structures 6, the adjustability of the arm 3 is stepped.

FIG. 4 shows an infinitely variable design of the pivot joint. In this embodiment a clamp screw 18 passing through a bent slot hole 19 and being directly or indirectly screwed with the vise 1 is provided instead of the bolt 5. The slot hole 19 is not provided with engagement structures but includes smooth side walls and its curvature and position relative to the pivot axis 2 corresponds to that of the slot hole 15 of the embodiment illustrated in the FIGS. 1 to 3. On the side of the arm 3 opposing the vise 1 the clamping screw 18 is widened into a shoulder having a diameter larger than the inner dimension of the oblong hole 19. The arm 3 is clamped and locked between the vise 1 and the shoulder of the clamping screw 18 by tightening the clamping screw 18. The locking takes place by force closure.

Another difference of the embodiment shown in FIG. 4 from that of the FIGS. 1 to 3 consists in the fact that the longitudinal profile 4 is not configured to have the cross-section of a standardized side rail of an operating table but as a round rod 20 including limit stops 21 on both sides as well as including recesses 22 or flattened portions 22. The end stops 21 prevent auxiliary equipment from inadvertently slipping off the round rod 20. The recesses 22 enable auxiliary equipment to be mounted to and dismounted from the round rod 20, wherein the auxiliary equipment is designed according to the lock-and-key principle matching the recesses 22 and can be mounted or dismounted in the area of said recesses 22 only. As a matter of course, it is within the scope of the invention that the round rod 20 according to FIG. 4 is combined with the stepped locking according to FIGS. 1 to 3 and the continuous locking according to FIG. 4 is combined with the longitudinal profile 4 according to FIGS. 1 to 3.

Except for the two afore-mentioned differences, the adapter device of FIG. 4 otherwise corresponds to the adapter device shown in FIGS. 1 to 3.

The invention claimed is:

1. An adapter device for releasable mounting of instruments and equipment on a side rail of an operating table, the adapter device comprising:
    a clamping device that clamps the adapter device to the side rail of the operating table,
    a longitudinal profile on which instruments and equipment are to be detachably fastened, and
    a lockable joint which is equipped with at least one pivoting degree of freedom around a pivoting axis and is arranged between the clamping device and the longitudinal profile so that the longitudinal profile can be aligned relative to the clamping device, wherein
    the lockable joint is adapted to be locked by a form closure in that a locking bolt being arranged offset from but parallel to the pivoting axis of the lockable joint detachably engages in a locking recess or in one of a plurality of locking recesses of the lockable joint, said locking bolt being operable by a first handle and the clamping device being operable by a second handle separately and independently from the operation of the locking bolt.

2. The adapter device according to claim 1, wherein the locking bolt is a spring-loaded tension bolt which, in an idle position into which the tension bolt is biased, engages the locking recess or in one of the plurality of locking recesses and can be released from said locking recess or said one of the plurality of locking recesses by pulling against a spring load of the tension bolt.

3. An adapter device for releasable mounting of instruments and equipment on a side rail of an operating table, the adapter device comprising:
    a clamping device by means of which the adapter device can be clamped to the side rail of the operating table,
    a longitudinal profile on which instruments and equipment are to be detachably fastened,
    and
    a lockable joint which is equipped with at least one pivoting degree of freedom and is arranged between the clamping device and the longitudinal profile so that the longitudinal profile can be aligned relative to the clamping device,
    wherein the lockable joint is adapted to be locked by means of force closure in that a clamping screw being arranged offset from but parallel to the pivoting axis of the lockable joint detachably clamps the lockable joint, said clamping screw being operable by a shoulder of the clamping screw and the clamping device being operable by a handle separately and independently from the operation of the clamping screw.

4. The adapter device according to claim 3, wherein the lockable joint allows for pivoting the longitudinal profile in a form of a pitch in a vertical plane.

5. The adapter device according to claim 3, wherein the adapter device is configured for an operating table comprising at least one segmented side rail, and wherein the length (LL) of the longitudinal profile is shorter than the length (LS) of the side rail segment to which the adapter device is fastened.

6. The adapter device according to claim 3, wherein the lockable joint is a pivot joint or a ball joint.

7. The adapter device according to claim 3, wherein the clamping device forms part of the lockable joint.

8. The adapter device according to claim 3, wherein the clamping device is a vise.

9. The adapter device according to claim 3, further comprising an arm arranged between the lockable joint and the longitudinal profile and supporting the longitudinal profile at a distance from the pivot axis of the lockable joint.

10. The adapter device according to claim 9, wherein the arm forms a free space adapted to be used as a handle for adjusting or adapting the adapter device.

11. The adapter device according to claim 3, wherein the longitudinal profile has a cross-section that corresponds to a cross-section of a standardized side rail of an operating table or is round.

12. The adapter device according to claim 3, wherein the clamping device includes a pressure plate which is adapted to be braced by a tightening screw vis-à-vis a side rail of the operating table.

13. The adapter device according to claim 3, wherein the longitudinal profile has end-side stops.

14. The adapter device according to claim 3, wherein the longitudinal profile includes flattened portions or indentations configured to engage with instruments and equipment that are arranged on the longitudinal profile.

* * * * *